(12) United States Patent
Kawato

(10) Patent No.: US 7,778,007 B2
(45) Date of Patent: Aug. 17, 2010

(54) OPTICAL EMISSION ANALYSIS APPARATUS

(75) Inventor: Eizo Kawato, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 825 days.

(21) Appl. No.: 11/686,103

(22) Filed: Mar. 14, 2007

(65) Prior Publication Data
US 2007/0247621 A1 Oct. 25, 2007

(30) Foreign Application Priority Data
Apr. 19, 2006 (JP) ............................. 2006-115114

(51) Int. Cl.
*F23Q 3/00* (2006.01)

(52) U.S. Cl. ....................................................... 361/254
(58) Field of Classification Search ................. 361/253, 361/254
See application file for complete search history.

(56) References Cited

U.S. PATENT DOCUMENTS 4,763,045 A * 8/1988 Choi et al. ............ 315/209 SC
6,191,537 B1 * 2/2001 Celso .......................... 315/219
6,584,965 B1 * 7/2003 Ward ........................... 123/605
6,734,637 B2 * 5/2004 Ellams ........................ 315/224
2002/0121866 A1 * 9/2002 Ellams ........................ 315/219

FOREIGN PATENT DOCUMENTS

JP             56-047564              4/1981

* cited by examiner

*Primary Examiner*—Ronald W Leja
(74) *Attorney, Agent, or Firm*—J.C. Patents

(57) ABSTRACT

An optical emission analysis apparatus includes a discharge gap, an ignitor circuit, and a main discharge power supply. The ignitor circuit includes an ignition transformer, a pair of current control devices, and an excitation power supply. On a secondary coil of the ignition transformer, the discharge gap and the main discharge power supply are connected in series to form a main discharge current path. On a primary coil of the ignition transformer, the pair of current control devices and the excitation power supply are connected in series to form an excitation current path. A pair of current control devices is connected to each other via mutually opposite polarities. The polarity of the high voltage generated in the secondary coil is reversed by reversing the polarity of the voltage of the excitation power supply. The direction of the main discharge current is reversed by reversing the polarity of the voltage of the main discharge power supply. Through the reverse polarity discharge, the deposits on the electrode are removed.

10 Claims, 2 Drawing Sheets

OPTICAL EMISSION ANALYSIS APPARATUS

CROSS-REFERENCE TO RELATED APPLICATION

This application claims the priority benefit of Japanese application no. 2006-115114, filed Apr. 19, 2006. All disclosure of the Japanese application is incorporated herein by reference.

BACKGROUND OF THE INVENTION

1. Field of the Invention

The present invention relates to an optical emission analysis apparatus, in which a discharging process is applied to evaporate atoms of a sample for emitting light; and the emission intensity is measured, so as to analyze elements of the sample. More particularly, the present invention relates to an optical emission analysis apparatus, in which a large-current spark discharge is produced between the metal sample and the discharge electrode, and an amount of elements is analyzed simultaneously in a short time.

2. Description of Related Art

In the optical emission analysis apparatus, the spark discharge is produced between the metal sample and the discharge electrode (discharge gap). The large-current discharge is used for evaporating the atoms on the surface of the metal sample, while the discharge plasma is used for exciting the atoms. Since each of the excited atoms and/or ions emits light according to the specific line spectrum of each element, the amount of elements existed in the plasma can be specified by introducing the light into a spectrometer and measuring the light intensity at a specific wavelength. By simultaneously measuring the light intensities with a plurality of wavelengths, the amount of various elements in the plasma can be determined. Thus, the relative amount of elements composing the metal sample can be specified.

In a conventional optical emission analysis apparatus (shown in FIG. 3), a main discharge power supply 12 and an ignitor circuit 13 are connected with a discharge gap 11 formed by a metal sample 32 and an electrode 31, so as to form a main discharge current path. In the main discharge power supply 12, a capacitor is charged to hundreds of volts (V). After the discharge begins in the discharge gap 11 (the gap between the metal sample 32 and the electrode 31), the energy for forming the large-current spark discharge is provided. A controller 14 controls the charging voltage and the timings of the main discharge power supply 12 and the ignitor circuit 13.

In order to avoid change of the surface condition of the sample during the analysis, a rare gas is usually filled in the gap between the metal sample 32 and the electrode 31. The metal sample 32 and the electrode 31 are arranged and spaced apart for approximately several millimeters (mm) to avoid causing a discharge at a voltage of hundreds of volts. The ignitor circuit 13 is used to apply a high voltage of approximately 10 kV, generated on the secondary coil of the ignition transformer 21, to the electrode 31, so as to start the discharge.

An excitation power supply 23 and a current control device 22 are connected to a primary coil of the ignition transformer 21, so as to form an excitation current path. Firstly, by turning on the current control device 22, the current flows from the excitation power supply 23 to the primary coil, so as to excite the primary coil. In the mean time, although the charged voltage in the capacitor of the main discharge power supply 12 has already been applied through a secondary coil of the ignition transformer 21, the discharge does not begin in the discharge gap 11 because the voltage is low.

When a predetermined current flows through the primary coil, by turning off the current control device 22, the secondary coil generates an induced voltage of more than 10 kV due to the magnetic energy accumulated in the ignition transformer 21. The insulation of the discharge gap 11 (the gap between the metal sample 32 and the electrode 31) is thereby destroyed to begin discharge.

Once the discharge begins, the main discharge power supply 12 supplies energy to the discharge gap 11 through the secondary coil of the ignition transformer 21, such that the discharge current rapidly increases, and a high-energy spark discharge occurs in the discharge gap 11. In the mean time, high temperature is formed at a part of the surface of the metal sample 32, such that the atoms of the sample begin to evaporate.

The evaporated atoms are excited by electrons in the plasma. When the excited atoms return to a stable state, the atoms emit lights with specific wavelength corresponding to the energy difference. Since each element has specific energy levels, the wavelengths of the light also form the line spectrum of the element. The emitted lights in the plasma are effectively introduced into the spectrometer, and the light intensities of elements are simultaneously measured. The ratio of light intensity of each wavelength is not solely proportional to the ratio of the corresponding elements. However, since the amount of each element is approximately proportional, by obtaining the relationship between the emission intensity and the amount of elements beforehand, the emission intensity can be converted to the amount of each element, so as to determine the composition of the elements.

However, the discharge conditions in the plasma generated by the spark discharge vary depending upon the surface condition of the sample. Accordingly, during a plurality of discharges, the amount of the evaporated element or the emission intensity is not constant, but varies randomly each time. Therefore, by repeatedly performing measurements for many times, and by integrating or averaging the signals of the emission intensity, the accuracy of the measured values can be improved. Furthermore, when the measurement begins, the emission intensity is not measured but only the discharge (pre-discharge) is performed. The surface conditions of the metal sample 32 and the electrode 31 await to become stable before the analysis is performed so as to improve the accuracy of the measured values.

The surface of the sample is stripped off due to the discharge. Therefore, after a suitable number of measurements has been performed, a fresh portion of the surface of the sample must be used for measurement, or the surface of the sample must be ground again. It should be noted that the discharge condition must be maintained constant as much as possible.

On the other aspect, the atoms evaporated from the surface of the metal sample 32 due to the discharge are attached on the surface of a peripheral insulator or the electrode 31. The part that cannot be seen from the discharge plasma is fabricated as an insulator to assure insulation. The electrode 31 always faces the metal sample 32 or the plasma surface. The deposits evaporated from the sample are attached on the top portion of the electrode 31, changing the discharge condition, and obstructing a normal discharge ultimately. Therefore, while the grinding of the sample is applied, the electrode 31 also needs to be ground. Therefore, aside from the analysis operation, additional maintenance operation is required, and the operation efficiency of the apparatus is reduced.

In the conventional art as disclosed in Patent Document 1, a technology of reversing the direction (polarity) of the main discharge current to eliminate the deposits on the electrode 31 is disclosed, wherein the burden of a grinding operation of the electrode 31 is obviated.

FIG. 4 is a schematic diagram of the optical emission analysis apparatus in the conventional art. In the structure of FIG. 3, the main discharge power supply 12 has a fixed polarity, whereas in the structure of FIG. 4 the main discharge power supply 15 capable of reversing the polarity is used. However, only by means of reversing the polarity of the main discharge power supply 15, a stable discharge cannot be obtained. Accordingly, an assistant discharge gap 24 is disposed in the ignitor circuit, so as to insulate the ignition transformer from the main discharge current path.

The voltage (discharge starting voltage) of the discharge gap 11, when the discharge begins, varies according to the momentary surface condition of the electrode 31 or the metal sample 32. The magnetic energy of the ignition transformer 21 must supply sufficient energy, such that the capacitive load on the secondary side is charged to generate a voltage higher than the discharge starting voltage when the magnetic energy of the ignition transformer 21 is converted to the electrostatic energy. Therefore, in the structure of FIG. 3, when the discharge begins, certain magnetic energy remains in the ignition transformer 21, so as to maintain a current with the same direction as that of the current when the discharge begins. Therefore, when the polarity of the voltage of the main discharge power supply is reversed, the main discharge current in the reverse direction cannot be effectively increased.

In FIG. 4, the ignition transformer 21 and the main discharge power supply 15 are connected in parallel, such that under the circumstance that the direction of the current when the discharge begins is different from that of the main discharge current, the spark discharge also can be stably improved. The ignition transformer 21 and the main discharge power supply 15 are connected in parallel, so the assistant discharge gap 24 is used to perform a DC insulation for the ignition transformer 21 and the main discharge power supply 15 for preventing the capacitor of the main discharge power supply 15 from discharging to the ignition transformer 21. Once a high voltage is generated in the ignition transformer 24, the insulation of the assistant discharge gap 24 is destroyed to apply a high voltage to the electrode 31. Then, the insulation of the discharge gap 11 is destroyed to start discharging. Once the discharge begins and the voltage of the electrode 31 drops, the discharge between the electrodes of the assistant discharge gap 24 is stopped. Only the main discharge current from the main discharge power supply 15 to the discharge gap 11 is increased, and the spark discharge is formed. In the optical emission analysis apparatus shown in FIG. 4, by reversing the polarity of the main discharge current, the deposits on the electrode 31 are eliminated. The burden for the grinding operation of the electrode 31 is thus obviated.

[Patent Document 1] Japanese examined Utility Model Publication No. 56-47564.

In the conventional optical emission analysis apparatus, since a plurality of spark discharges is performed, the deposits evaporated from the sample 32 are formed on the electrode 31. The grinding operation of the electrode 31 to eliminate the deposits becomes a burden. In the conventional art shown in FIG. 4, the deposits on the electrode 31 are eliminated by means of reversing the polarity of discharge, and the grinding operation of the electrode 31 is thereby obviated.

Although the current in the assistant electrode gap 24 is relatively small, the discharge current flows through the assistant electrode gap 24 as the current through the discharge gap 11. So, the electrodes of the assistant electrode gap 24 must also be ground. Although the frequency for performing the grinding operation of the electrode is low, additional maintenance operation aside from the analysis operation is required. Thus, the operation efficiency of the apparatus is reduced.

SUMMARY OF THE INVENTION

Accordingly, the present invention is directed to an optical emission analysis apparatus, which comprises a discharge gap, an ignitor circuit, and a main discharge power supply. The ignitor circuit is used to start discharge in the discharge gap, and the main discharge power supply is used to maintain discharge in the discharge gap. The ignitor circuit comprises an ignition transformer, a pair of current control devices, and an excitation power supply. On a secondary coil of the ignition transformer, the discharge gap and the main discharge power supply are connected in series to form a main discharge current path. On a primary coil of the ignition transformer, the pair of current control devices and the excitation power supply are connected in series to form an excitation current path. The pair of current control devices is connected to each other via mutually opposite polarities.

Furthermore, in the optical emission analysis apparatus of the present invention, the polarity of the high voltage generated in the secondary coil of the ignition transformer is reversed by reversing the polarity of the voltage of the excitation power supply.

Furthermore, in the optical emission analysis apparatus of the present invention, at the time when the polarity of the voltage of the excitation power supply is reversed, the direction of the main discharge current is also reversed by reversing the polarity of the voltage of the main discharge power supply.

Furthermore, in the optical emission analysis apparatus of the present invention, the current control device is formed by one or more power switching devices connected in parallel.

Furthermore, in the optical emission analysis apparatus of the present invention, the excitation power supply circuit is formed with a capacitor and a charging circuit. Further, the polarity of the charging voltage of the capacitor is switched according to the polarity of the high voltage generated on the secondary coil of the ignition transformer.

Through utilizing the optical emission analysis apparatus of the present invention, by reversing the direction of the main discharge current, the deposits on the electrode 31 are removed to obviate the grinding operation of the electrode 31. In addition, since the assistant electrode gap is not used, no additional performance of an electrode grinding operation is required.

Since the frequency of performing the grinding operation for electrodes is greatly reduced, no additional maintenance operations is required besides the analysis operation. Thus, the operation efficiency of the apparatus is increased.

In order to achieve the aforementioned and other objects, features and advantages of the present invention comprehensible, preferred embodiments accompanied with figures are described in detail below.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
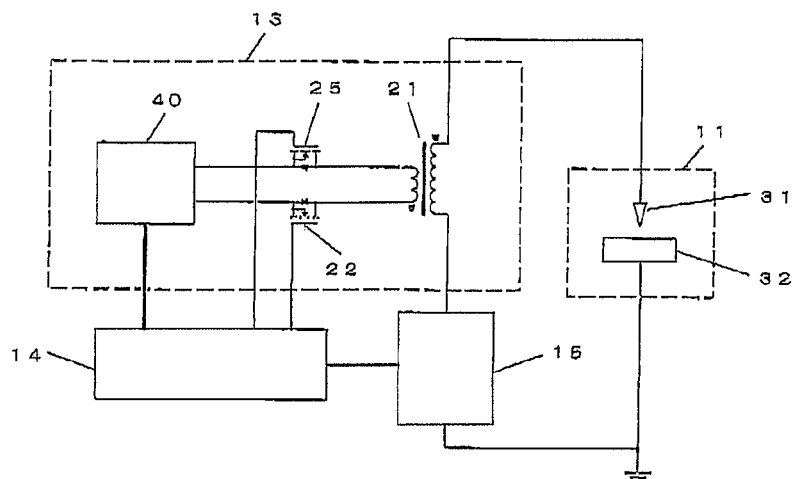
FIG. 1 is a schematic diagram of an optical emission analysis apparatus according to an embodiment of the present invention.
Figure 3:
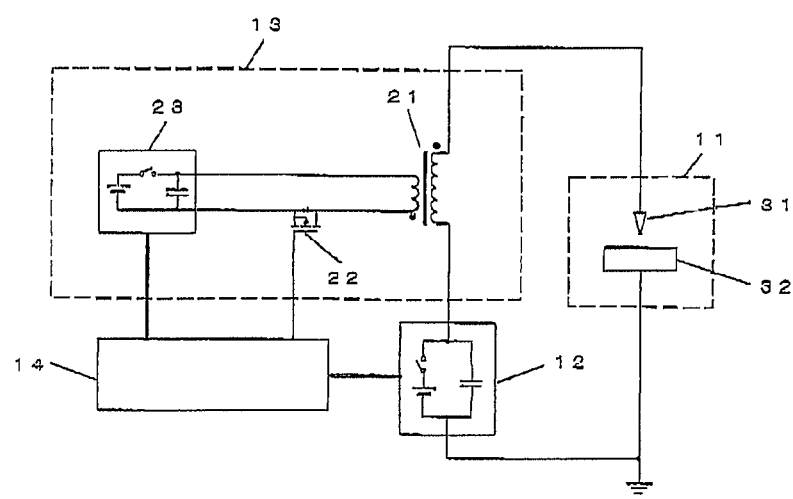
FIG. 3 is a schematic diagram of an optical emission analysis apparatus in the conventional art.
Figure 4:
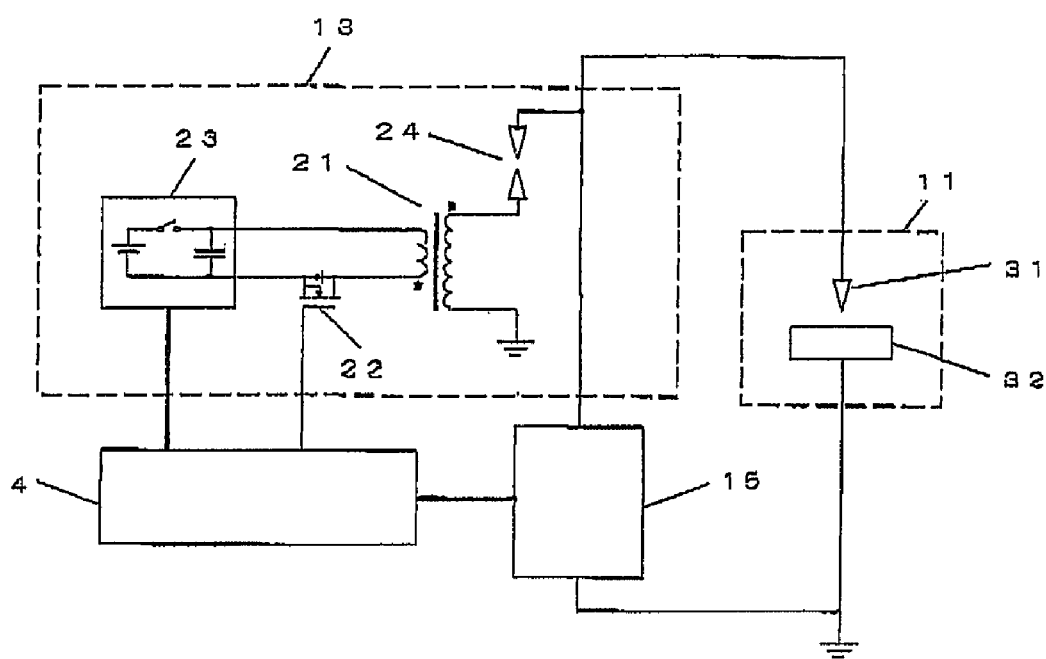
FIG. 4 is a schematic diagram of another optical emission analysis apparatus in the conventional art.

The detailed illustration of the optical emission analysis apparatus of the present invention is provided below with reference to the drawings. FIG. 1 is an example of a schematic diagram of an optical emission analysis apparatus. In FIG. 1, the same reference numbers are used to refer to the same or like parts of the conventional optical emission analysis apparatus illustrated in FIGS. 3 and 4. The structure of the apparatus in this embodiment is similar to that of the optical emission analysis apparatus shown in FIG. 3. A main discharge power supply 15 and an ignitor circuit 13 are connected with a discharge gap 11 formed by a metal sample 32 and an electrode 31 to form a main discharge current path. In the main discharge power supply 15, the capacitor is pre-charged to hundreds of volts (V). After the discharge begins in the discharge gap 11 (the gap between the metal sample 32 and the electrode 31), the energy used to form the large-current spark discharge is supplied. The controller 14 controls the charging voltage and the timing, and the voltage polarity of the main discharge power supply 15 and the ignitor circuit 13.

On the primary coil of the ignition transformer 21, an excitation power supply 40 and a pair of current control devices 22 and 25 are connected in series to form an excitation current path. The pair of current control devices 22 and 25 is connected to each other via mutually opposite polarities. In FIG. 1, as an example of the current control device, a metal-oxide-semiconductor field-effect transistor (MOSFET) is used, or another current control device such as an insulated gate bipolar transistor (IGBT) can also be used. In addition, in order to increase the current, a device with a plurality of elements such as MOSFETs or IGBTs connected in parallel can be used as one current control device. In this embodiment, drain terminals of the pair of current control devices 22 and 25 are connected to two terminals of the primary coil of the ignition transformer 21. As long as the current control devices 22 and 25 are reversely disposed along the excitation current path, both devices may be connected on one side of the ignition transformer 21 in principle. However, in order to reduce the voltage change at the control terminal of the current control devices 22 and 25 or the excitation power supply 40 when a high voltage is generated on the ignition transformer 21, it is preferred that both drain terminals of the MOSFETs are connected to the primary coil of the ignition transformer 21, as shown in FIG. 1.

Figure 2:
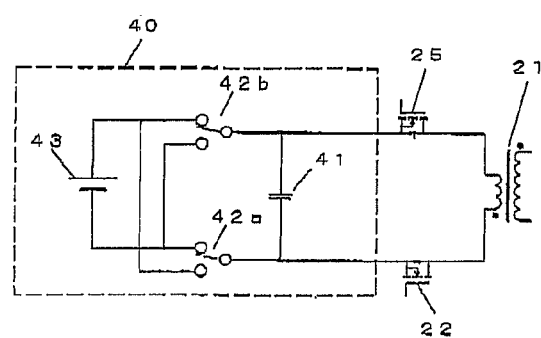
FIG. 2 is a structure diagram of an ignitor circuit for the optical emission analysis apparatus according to an embodiment of the present invention.

FIG. 2 shows an example of the structure of the excitation power supply 40. The excitation current of the ignition transformer 21 is supplied from a capacitor 41 to the primary coil through the pair of current control devices 22 and 25. Therefore, the capacitor 41 needs to be charged to a suitable voltage before the excitation is performed. Furthermore, when the polarity of the discharge current is reversed, the charging voltage of the capacitor 41 also needs to be reversed. Therefore, the capacitor 41 is connected with charging-polarity switches 42a and 42b and a charge power supply 43. Although it is not clearly shown in FIG. 2, the charge power supply 43 further includes elements used to control the timing for charging, such as an analog switch and a relay, which control the charging voltage or the charging polarity, and the timing for charging corresponds to the timing of the signal of the controller 14.

The actions of the ignitor circuit 13 under the polarity state of the charging-polarity switches 42a and 42b as shown in FIG. 2 are illustrated. After pre-charging the capacitor 41, the current control device 22 is turned on. If the current control device 25 is an MOSFET, etc., a body diode, which is generally associated, is automatically in the conductive state with respect to the polarity of the switches 42a and 42b, whereas in order to prevent the loss caused by the forward voltage drop, a gate voltage can be operated to turn on the MOSFET. Alternatively, if the body diode is not associated, and a current control device that is not automatically conductive, the current control device 25 should be actively turned on.

When the current of the primary coil reaches the predetermined current value, the current control device 22 is turned off. The excited ignition transformer 21 charges the load capacitor including a capacitor between windings or a stray capacitor of the primary coil or the secondary coil, and magnetic energy is gradually reduced. In order for the secondary coil to generate a high voltage, the number of turns of the secondary coil must be increased, so the effect of the capacitor at the secondary winding is increased. Thus, the capacitance must be reduced as much as possible. Once a sufficient high voltage is generated in the discharge gap 11 connected with the secondary coil, the insulation of the discharge gap 11 (the gap between the metal sample 32 and the electrode 31) is broken and the discharge begins.

The voltage when the discharge begins varies each time depending upon the surface condition, etc., of the electrode 31 or the metal sample 32. Consequently, the excitation energy of the ignition transformer 21 is excessively supplied. Therefore, after the discharging begins, the remaining magnetic energy can be used to maintain the current. On the main discharge power supply 15, since a voltage at the direction for increasing the current is applied, the discharge current is increased with time, and the spark discharge with a high energy occurs in the discharge gap 11.

In order to evaporate atoms of the sample, the main discharge current needs to be increased, and the surface of the metal sample 32 is heated to a high temperature in a short time. Therefore, an inductance of the secondary coil of the ignition transformer 21 must be as small as possible. In addition, in order to control the voltage on the primary coil, when a high voltage is generated on the secondary coil, to be a practical voltage (for example, 1 kV) for the current control devices 22 and 25, the inductance of the primary coil is made smaller. Therefore, in order to obtain the required excitation energy, the excitation current flowing in the primary coil is set to be a large current of over 100 A.

Thus, in the primary coil for generating the high voltage and the large current, it is impossible, considering from the voltage rating or the current rating, to use a standard relay etc., to switch the polarity of the current. The current control devices 22 and 25, such as the MOSFET, are easier to control a large current of over 100 A, but these devices are usually designed to be used with a polarity. Therefore, if the pair of current control devices 22 and 25 is reversely connected along the excitation current path, as shown in FIG. 1 or FIG. 2, then under the condition when the polarity of the current is switched, one of the current control device can cut off the current, and can sustain the high voltage generated on the drain terminal. The source terminal connected to the excitation power supply 40 or the gate terminal connected to the controller 14 may not be affected by a high voltage pulse of, for example, approximately 1 kV generated on two terminals of the primary coil. Thus, erroneous operations can be prevented.

When an opposite polarity discharge is performed in order to remove the deposits adhered on the electrode 31, the charging voltage of the main discharge power supply is reversed. And the voltages of the charging-polarity switches 42a and 42b are switched, so as to reverse the charging voltage of the capacitor 41 in the excitation power supply 40. Then, by turning on the current control device 25, the excitation current will flow in a reverse direction. In a mean time, as described above, it is feasible so long as the current control device 22 is made conductive. By turning off the current control device 25, the polarity of the high voltage generated on the secondary coil of the ignition transformer 21 is also reversed, and the main discharge power supply 15 charged by the reversed polarity forms the spark discharge with the reversed main discharge current.

Thus, by utilizing the optical emission analysis apparatus of the present invention, it is easy to generate the spark discharge of reversed polarity, so as to eliminate the deposits evaporated from the sample and attached on the top portion of the electrode 31. Furthermore, since the assistant discharge gap is not used, no electrode grinding operations of the assistant discharge gap is required. Therefore, the frequency of performing the electrode grinding operation is greatly reduced, such that no additional maintaining operation besides the analysis operation is generated. Ultimately, the operation efficiency of the apparatus is improved.

The above embodiment is only an example of the present invention, and definitely, the technology suitably varied or modified within the spirit of the present invention is also included in the present invention.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An optical emission analysis apparatus, comprising a discharge gap, an ignitor circuit, and a main discharge power supply, wherein the ignitor circuit is used to start a discharge in the discharge gap, and the main discharge power supply is used to maintain the discharge in the discharge gap;

wherein the ignitor circuit comprises an ignition transformer, a pair of current control devices, and an excitation power supply;

on a secondary coil of the ignition transformer, the discharge gap and the main discharge power supply are connected in series to form a main discharge current path;

on a primary coil of the ignition transformer, the pair of the current control devices and the excitation power supply are connected in series to form an excitation current path; and the pair of the current control devices is connected to each other via mutually opposite polarities.

2. The optical emission analysis apparatus as claimed in claim 1, wherein a polarity of a high voltage generated in the secondary coil of the ignition transformer is reversed by reversing a polarity of a voltage of the excitation power supply.

3. The optical emission analysis apparatus as claimed in claim 1, wherein a direction of a main discharge current is reversed by reversing a polarity of a voltage of the main discharge power supply, while reversing a polarity of a voltage of the excitation power supply.

4. The optical emission analysis apparatus as claimed in claim 1, wherein the current control device is formed by one or more power switching devices connected in parallel.

5. The optical emission analysis apparatus as claimed in claim 1, wherein the excitation power supply circuit is formed by a capacitor and a charging circuit, and a polarity of a charging voltage of the capacitor is switched, according to a polarity of a high voltage generated on the secondary coil of the ignition transformer.

6. The optical emission analysis apparatus as claimed in claim 3, wherein the optical emission analysis apparatus does not include an assistant electrode gap and an additional electrode grinding operation is not performed.

7. The optical emission analysis apparatus as claimed in claim 1, wherein on two terminals of the primary coil of the ignition transformer, drain terminals of the pair of the current control devices are connected.

8. The optical emission analysis apparatus as claimed in claim 5, wherein an excitation current of the ignition transformer is supplied from a capacitor to the primary coil through the pair of the current control devices.

9. The optical emission analysis apparatus as claimed in claim 8, wherein charging polarity switches and a charging power supply are connected on the capacitor.

10. The optical emission analysis apparatus as claimed in claim 9, wherein the charging polarity switch includes elements comprising analog switches or relays, for controlling a polarity of charging.

* * * * *